United States Patent [19]
Gendler

[11] Patent Number: 5,092,887
[45] Date of Patent: Mar. 3, 1992

[54] ARTIFICIAL LIGAMENT PRODUCED FROM DEMINERALIZED BONE FOR THE REPLACEMENT AND AUGMENTATION OF LIGAMENTS, TENDONS AND OTHER FIBROUS CONNECTIVE TISSUE

[76] Inventor: El Gendler, 917 S. Shenandoah, Los Angeles, Calif. 90035

[21] Appl. No.: 743,835

[22] Filed: Aug. 12, 1991

[51] Int. Cl.⁵ ................................................ A61F 2/08
[52] U.S. Cl. ......................................... 623/13; 623/66
[58] Field of Search .................................. 623/13, 66

[56] References Cited
U.S. PATENT DOCUMENTS
4,932,973  6/1990  Gendler ................................. 623/16

Primary Examiner—David Isabella
Assistant Examiner—Debra S. Brittingham
Attorney, Agent, or Firm—Leydig, Voit & Mayer

[57] ABSTRACT

A method for the replacement or augmentation of a damaged fibrous connective tissue in a region between first and second body parts. The method comprises attaching artificial ligaments made from demineralized bone between said first and second body parts, said artificial ligament having a thickness such that it has sufficient flexibility to allow it to be shaped to conform to the configuration of the region to be repaired and strength sufficient for the intended application.

10 Claims, No Drawings

ARTIFICIAL LIGAMENT PRODUCED FROM DEMINERALIZED BONE FOR THE REPLACEMENT AND AUGMENTATION OF LIGAMENTS, TENDONS AND OTHER FIBROUS CONNECTIVE TISSUE

BACKGROUND OF THE INVENTION

Ligaments and tendons are bands or sheets of fibrous connective tissue which provide support and stability to the musculoskeletal system. Unfortunately, injury and damage to a ligament or tendon is a frequent occurrence. Such injuries include those to the shoulder rotator cuff and ligaments of the knee, such as the anterior cruciate, and medial and lateral collateral, and acromioclavicular separations. Additional injuries include those to the lateral collateral ligaments of the ankle and to the large tendons, such as the achilles, quadriceps and patellar tendons, and the small tendons, such as flexor and extensor tendons of the hand.

Relief of the pain and/or instability caused by damage to a ligament or tendon is currently achieved by techniques ranging from simple suturing to removal and replacement with other tissue or a permanent synthetic prosthesis, depending upon the severity of the damage.

The state-of-the-art in severe ligament repair/reconstruction is considered to be the use of autogenous and allogeneic tissue grafts for augmentation or replacement of the damaged ligament. As an alternative to autogenous and allogeneic tissue grafts, xenografts, tissue grafts from a species other than the recipient species, have been implanted to replace natural ligaments. Xenografts have tended to be unpredictable in the long term for restoring full strength and stability to the involved joint.

Portions of the patellar tendon, iliotibial band, semitendinosus tendon, and fascia lata are some of the most commonly used autogenous and allogeneic tissue grafts. An example of such a procedure in the knee is the reconstruction of the anterior cruciate ligament by using a portion of the patellar tendon. Other tendons such as the semitendinosus tendon, and connective tissues such as fascia lata, are sometimes used to reconstruct the damaged ligament. Due to the undesirability of having to sacrifice one tissue and its associated function, in order to repair another, a number of synthetic, permanent total ligament prostheses and ligament augmentation implants have been tried. The medical community has prescribed certain characteristics for prosthetic ligaments. While all the properties influencing the ultimate success of a ligament prosthesis have not yet been defined, the following are some of the most important desired characteristics:

1. Adequate strength;
2. Resistance to elongation;
3. Fixation methods, the device should be easy to implant and attach;
4. Biocompatability, as demonstrated by a minimum of inflammatory responses;
5. Longevity, the device should last the lifetime of the patient;
6. Tissue ingrowth, host tissue should be able to penetrate the device to stabilize and ultimately enhance the device's physical property;
7. Activity, the implanted device should allow early if not immediate use of the limb;
8. Pliability;
9. Resistance to abrasion.

Several permanent, nonaugmented prosthetic ligaments have been developed. A permanent prosthesis is one which assumes its full strength initially upon implantation, is not intended to gradually resorb or disintegrate over time and does not depend on autografts or "regrown" natural ligament tissue for its ultimate success. Dore et al. U.S. Pat. No. 4,301,551, which issued on Nov. 24, 1981 describes a deformable silicone core surrounded by a tensionable wrapping of polymeric or stainless steel threads wound in a helical angle about the core. The core is the load bearing member and is capable of large elastic deformation in response to compression by the threads when the device is stretched. Two rigid plastic or stainless steel rods, one at each end of the core, connect the device to the bones of a joint.

A number of techniques employing carbon fiber-type or polypropylene augmentation devices are described in Vol. 196 of CLINICAL ORTHOPAEDICS AND RELATED RESEARCH, SYNTHETIC LIGAMENTS AND TENDONS, (H. Alexander & A. Weiss eds. June 1985). For example, a flat strap-like braid of polypropylene fibers was used to augment natural tissue grafts in studies conducted on goats. See G. McPherson et al. "Experimental Mechanical and Histologic Evaluation of the Kennedy Ligament Augmentation Device", CLINICAL ORTHOPAEDICS supra, p. 186. The time required for the recipient to return to normal activity is generally about one year or longer.

Treace U.S. Pat. No. 3,953,896, which issued on May 4, 1976 describes a prosthetic ligament made of a flexible, ultra high molecular weight polyethylene rod. Stainless steel sleeves and polyethylene nuts on each end of the flexible rod hold the prosthetic ligament to the bones.

Several of the permanent ligament prostheses are fabricated so that the properties of a single synthetic material characterize the implant's response to in vivo loading (see, e.g., U.S. Pat. Nos. 3,896,500; 3,953,896; 3,987,497; 3,988,783; and European Patent Application Nos. 51,954; 106,501; and 126,520, all of which are incorporated herein by reference).

Dahlen et al. U.S. Pat. No. 4,187,558, which issued on Feb. 12, 1980, describes a flexible braid made of Dacron (polyethylene terephthalate), encased in silicone rubber. A velour covered collar at one or both ends of the braid aids in attachment to the bone and promotes bone ingrowth to anchor the device.

A number of multi-component ligament prostheses (see, e.g. U.S. Pat. Nos. 3,797,047; 4,187,558; 4,483,023; and European Patent Application No. 122,744, all of which are incorporated herein by reference), are more bio-mechanically compatible with the elasticity and strength requirements of natural ligament function but suffer from other shortcomings. Since they are designed to replace the natural ligament, any reparative tissue that forms at the site of the defect, is almost completely shielded from applied loads and therefore tends to resorb.

Attempts at a long-term 'natural' tissue repair (by augmenting but not replacing the natural tissue) has been approached by the use of a variety of devices and techniques. The use of a permanent device for augmentation of an autogenous tissue transplant is described in "Experimental Mechanical and Histologic Evaluation of the Kennedy Ligament Augmentation Device", G. K. McPherson, Ph.D. et al., Clinical Orthopedics and Related Research, Vol. 196, pages 186 to 195, 1985, which is incorporated herein by reference. While the method of attachment allows the desired natural tissue repair to occur, the entire synthetic implant remains in situ; some interfibrillar mechanical breakdown has been reported, and a chronic foreign body response is observed even at 2 years following implantation. A biologically mechanically degradable augmentation device consisting of polyglycolic acid (herein abbreviated as PGA) -coated carbon fibers (U.S. Pat. No. 4,411,027) or polylactic acid (herein abbreviated as PLA) - coated carbon fibers (U.S. Pat. No. 4,329,743) has also met with limited success in obtaining a 'natural' tissue ligament repair.

Artificial ligaments and tendons made of bundles, interwoven or plated, and consisting of plastic fibers or of carbon fibers, coated with a substance absorbable inside the body are known in the art for tissue augmentation. For example, a flat strap-like braid of polypropylene fibers was used to augment natural tissue grafts in studies conducted on goats. See G. McPherson et al., "Experimental Mechanical and Histologic Evaluation of the Kennedy Ligament Augmentation Device", CLINICAL ORTHOPAEDICS, supra, p. 186. The time required for the recipient to return to normal activity is generally about one year or longer.

Another nonaugmented prosthetic ligament reported by C. Bolton and W. Bruchman, "The GORE-TEX Expanded Polytetrafluoroethylene Prosthetic Ligament", CLINICAL ORTHOPAEDICS, Vol. 196, p. 202, is constructed of bundles of Gore-Tex fibers arranged in a braided configuration. The braid is fixed by bone screws placed through eyelets at each end of the braid. Zachariades U.S. Pat. No. 4,587,163 discloses an isotropic semicrystalline morphology of ultra high molecular weight polyethylene for use in making artificial tendons or ligament prostheses. The artificial tendon can be sutured to a natural tendon segment. The polyethylene described by Zachariades is an ultradrawn melt crystallized ribbon-like structure.

One device, described in U.S. Pat. No. 4,483,023 by Hoffman, et al., comprises a knitted polyester sheath surrounding a core of polyester strands.

U.S. Pat. No. 4,149,277 introduces another variant in the construction of prosthetic ligaments and tendons in the form of carbon coated polyester filaments in braided, woven or meshed array.

U.S. Pat. No. 4,585,458 describes the use of chemically fixed heterologous collagenous tissues instead of synthetic materials for repair or replacement of ligaments or tendons. At present such devices have not proven to be effective alternatives for ligament repair since they typically exhibit premature failure.

All of the aforementioned tissue replacement and/or augmentation approaches suffer from various deficiencies. A problem associated with the autogenous transplant methods for ligament reconstruction relates to damage and loss of strength of the donor structure. During the healing process these donor tissues eventually regain their strength. However, until the strength of the tissues is recovered, they must be protected from carrying normal loads. Therefore, these procedures are accompanied by long rehabilitation regimens.

The synthetic prosthetics also suffer from certain deficiencies. While ligamentous tissue is a natural composite material exhibiting both compliant elasticity and high longitudinal strength, no single synthetic biocompatible material has this combination of properties. The inevitable chemical and/or physical breakdown of these implants in vivo, leads to catastrophic failure and a return to pre-operative instability, or worse, because no natural tissue repair has taken place. As a result, implants such as the ones listed above have tended to fail in animal or clinical trials either by material fatigue, creep, or in-vivo degradation leading to joint laxity, or by unacceptable restriction of joint motion.

As mentioned above, one problem often experienced by recipients of some prosthetic ligaments is that the braided ligaments undergo constructional deformation after implantation and, as a result, become too lax over time. Constructional deformation occurs when the fibers of the braided ligament prosthesis compact and undergo helical changes. There is a certain amount of "slack" in the prosthetic ligaments heretofore available which permits them to undergo constructional deformation with use. The prosthetic ligament lengthens and loses its tensioning capacity.

Also, as a result of the contact of yarns in braided, woven, or meshed constructions, ultimately a delamination of carbon from these points could occur, thus reducing the biocompatability of the device.

The mechanical properties of carbon fibers used at present predominantly for implants are strongly non-isotropic, due to the graphitic structure of carbon. Bending loads or stresses with small radii of curvature, or even relatively slight shearing stresses, may cause fibers to fracture. Furthermore, carbon fibers have only low ductility and tend to crumble, particularly if their coats have been dissolved after a longer stay inside the body.

No ligament prosthesis, tried thus far in animals or humans, has yielded consistently acceptable joint stability without the occurrence of implant breakdown, synovitis, and/or articular tissue damage during the first two years post operatively. The desired minimum post operative period of implant/joint stability is 10 years.

It is clear that there remains a significant need for a method for achieving a ligament replacement or augmentation having initial and long-term strength, flexibility, extension and recovery that at least approximate those of the original, undamaged ligament or other fibrous connective tissue.

SUMMARY OF THE INVENTION

It has now been surprisingly discovered that completely or partially demineralized cortical bone can be sliced in strips and rods and that such strips and rods have totally unexpected properties. The strips and rods have compliant elasticity and longitudinal strength similar to natural ligaments and tendons. Thus, the present invention provides artificial ligaments produced from demineralized cortical bone which are useful for in vivo replacement, repair and augmentation of damaged ligaments, tendons or other fibrous tissue that permanently connects first and second body members such as the femur and tibia.

Furthermore, the present invention provides a method for the replacing, repairing or augmenting of damaged ligament, tendon or other fibrous tissue that permanently connects first and second body members, such as the femur and tibia. The result of the present invention is a permanent replacement for a natural tendon, ligament or other fibrous tissue. The recipient of the treatment of the present invention can return to a normal range of activity much more quickly than the recipient of autogenous ligaments. Furthermore, the mechanical parameters of strength, flexibility, extension of recovery provided by the present invention, unlike synthetic prosthetic ligaments, at least approximate those of the original, undamaged natural ligament.

The present invention provides a method for the replacement or augmentation of a damaged fibrous connective tissue in a region between first and second body parts. The method comprises attaching artificial ligaments made from demineralized bone between said first and second body parts, said demineralized bone having a thickness such that it has sufficient flexibility to allow it to be shaped to conform to the configuration of the region to be repaired and tensile strength sufficient for its intended application.

Thus, the present invention provides an artificial ligament made from demineralized bone and a method for fibrous connective tissue replacement or augmentation that achieves adequate strength; resistance to elongation; ease of fixation; biocompatability; early use of the limb; pliability; and resistance to abrasion.

In accordance with the present invention, demineralized bone is employed to create artificial ligaments. The demineralized bone generally is used in the form of thin strips and rods that are flexible, while exhibiting significant tensile strength. Membranes made from such demineralized bone are disclosed in copending application Ser. No. 07/606,449, filed Oct. 31, 1990.

Thus, the present invention provides an artificial ligament made from demineralized bone and a method for the replacement or augmentation of damaged fibrous tissue by attaching artificial ligament made from demineralized bone between first and second body parts, such as the femur and tibia. The demineralized natural bone has a thickness such that it has sufficient flexibility to allow it to be shaped to conform to the configuration of the region to be repaired and tensile strength sufficient for its intended application.

Other advantages of the present invention will be more readily apparent upon reading the following description of the preferred exemplified embodiment of the invention.

DETAILED DESCRIPTION OF THE PREFERRED EMBODIMENTS

While the present invention will be described in connection with certain preferred embodiments, it is not intended that the present invention be so limited. On the contrary, it is intended to cover all alternatives, modifications, and equivalent arrangements as may be included within the spirit and scope of the invention as defined by the appended claims.

The present invention employs a novel artificial ligament for fibrous, connective tissue replacement and/or augmentation. The ligament comprises a continuous strip of demineralized natural bone having a predetermined and therapeutically advantageous thickness. This material is biocompatible, noninflammatory, and has the ability to be ultimately readsorbed by the body and replaced with natural, fibrous connective tissue.

This replacement process is possible because the demineralized bone allows undifferentiated cells to ingrow into the matrix, after implantation, and those undifferentiated cells, in turn, transform into differentiated fibroblasts which deposit collagen fibers, thus providing additional strength to the region.

Further, the aforementioned ligament surprisingly is flexible while retaining its structural and dimensional integrity both prior to and after hydration and additionally possessing significant tensile strength. Thus, the artificial ligament made from demineralized bone when connected to two body members, such as the femur and tibia, provides sufficient initial strength to allow a patient a degree of initial mobility.

Further, after a period of a few months, the generation of new connective tissue, induced by the presence of the demineralized bone, will provide sufficient strength for the patient to have normal mobility.

Although demineralized bone heretofore has existed in the art, no one has previously used demineralized bone for such an application. Indeed, it is quite surprising and unexpected that an artificial ligament made of demineralized bone could be used in such an application that requires the initial implant to have both significant flexibility and tensile strength. Nothing in the art heretofore indicated that artificial ligaments made from demineralized bone could exhibit such a desirable combination of flexibility and tensile strength. Additionally, as indicated above, the use of the demineralized bone allows for significant new fibrous tissue growth to be achieved, thus restoring the patient to nearly the same degree of flexibility and strength as existed before the damage to the fibrous connective tissue, such as a ligament in the knee.

The demineralized bone employed in the present invention may be used in conjunction with other classical approaches to ligament repair, such as the use of tissue transplants (such as the fascia lata) and/or synthetic prostheses.

The demineralized bone strip itself may be produced from any natural bone, of human or animal origin. Generally, the bone material is first harvested from any suitable vertebrate. The harvested material may be further processed by various techniques to remove substantially all blood and lipid residue. The resulting bone may be cut into strips and rods of approximately 0.1-1.5 cm width and 0.1-1.5 cm in thickness. Cutting of the bone should be undertaken with continuous irrigation of the blade to prevent unwanted heating of the bone. The resulting strips and rods may be further processed to remove any remaining blood and lipids, as by treatment with organic solvents for lipid extraction.

Demineralization of the bone is subsequently conducted by any known method, e.g., subjecting the bone to different acids, chelating agents, electrolysis or any combination of the foregoing, all as is well known in the art.

Additionally, the bone material may be treated with various chemical agents, such as hydrogen peroxide and with enzymes for modification of the mechanical properties and chemical composition of the bone structure components.

It has been discovered that the aforementioned artificial ligament made from demineralized bone, when machined to a certain dimension, 0.1-1.5 cm wide and 0.1-1.5 cm thick, allows for substantial new fibrous tissue formation throughout its thickness. Ultimately, the bone is completely readsorbed by the living system into which it is implanted and becomes replaced by fibrous tissue with the structure similar to natural ligaments and tendons.

Further, the demineralized bone is flexible, while having sufficient tensile strength. Generally, the thickness at which this will occur ranges from about 0.1 cm and up to 1.5 cm. Advantageously, the thickness will range from about 0.3 to about 1.3 cm, and the thickness preferably ranges from about 0.5 to about 1.0 cm.

In accordance with the aforesaid dimensions, artificial ligaments made from demineralized natural bone having any desired length, typically from about 5 cm to about 20 cm, and width from about 0.1 cm to about 1.5 cm may be produced, this being limited only by the dimensions of the bone material supplied. The material may then be reduced to the desired length and width dimensions by cutting.

The surgical procedures used to implant the artificial ligaments are all well known in the art. The method of the present invention may be employed to repair injuries to the shoulder rotator cuff and ligaments of the knee, such as the anterior cruciate, and medial and lateral collateral, and acromioclavicular separations. Additional injuries that may be repaired include those to the lateral collateral ligaments of the ankle and to the large tendons such as the achilles, quadriceps and patellar tendons, and small tendons such as flexor and extensor tendons of the hand.

The method of the present invention may be used in conjunction with other recognized methods of ligament repair, such as of fascia lata, patella-tibial ligament, achilles tendon (all allografts and autografts), synthetic artificial ligaments.

Although the present material and methods are useful in humans, they will also be found useful in treating many different types of animals, e.g., horses, dogs and the like.

EXAMPLE 1

Repair of Acromioclavicular ("Shoulder" or "A-C") Separation by Augmenting the Fibrous Tissue of the A-C Joint Capsule This common injury results in rupture of the joint capsule between the clavicle (collar bone) to the scapula (shoulder blade). It is somewhat disfiguring in the female and disabling in the male. Attempts to restore stability have included wrapping fascia, sutures, or synthetic around the clavicle and under the coracoid process, screwing the bones together, i.e., a Bosworth screw, and/or repairing the joint capsule of the acromio-clavicular ("A-C") joint. Repair of the capsule is difficult because of the limited tissue available for suture, and often requires augmentation for optimum fibrous tissue repair. Artificial ligament made from demineralized bone may be usefully employed. Because of its availability, minimum tissue response, shapability and strength, the artificial ligament of the present invention in appropriate form(s), offers several advantages over those presently available.

EXAMPLE 2

Repair of Torn Anterior Cruciate Ligament of the Knee by Replacement of the Ruptured Ligament This injury is often due to a sports related activity causing rupture of a thick round ligament which stabilizes the knee joint and yet allows freedom in bending. The resulting joint instability alone is disabling, but also makes the knee more susceptible to other injuries and arthritis. A number of approaches using autogenous fibrous tissue grafts, allogeneic ligament or fascia replacements, and synthetics (vide supra) have been attempted, with variably reported success. Fixation of these soft tissue or synthetic implants to the bones has been a difficult problem, and the tissue reaction incited by the several materials has detracted from their anticipated results. For the reasons listed in Example 1 above and the possibility of improved implant bone to host bone fixation with the artificial ligaments of the present invention, made from demineralized bone, improvement in the results of surgical replacement of anterior cruciate ligaments is possible.

EXAMPLE 3

Repair of Degenerative Rupture of Achille's Tendon by Combined Replacement and Augmentation The rupture of a degenerative Achille's tendon occurs in its substance almost spontaneously, usually in middle-aged males. Cause of the mocoid changes are not understood, but the resulting loss of strength leading to rupture and the lack of healthy tendon tissue for repair are observed facts. Consequently, reconstitution of the TENDON may be desirable but challenging. Autogenous graft fibrous tissue for suture or replacement, such as the plantaris tendon or fascia lata, requires additional surgical/anesthetic time, inflicting further trauma and increased risk of infection. For the reasons listed in Examples 1 and 2, it can be expected that the artificial ligament of the present invention, made from demineralized bone, will find new application in this difficult situation.

What I claim is:

1. A method for the replacement or augmentation of a damaged fibrous connective tissue in a region between first and second body parts, comprising attaching an elongated artificial ligament made from demineralized bone between said first and second body parts, said artificial ligament having both compliant elasticity and high longitudinal strength such that it has sufficient flexibility to allow it to be shaped to conform to the configuration of the region to be repaired.

2. The method of claim 1, wherein said ligament having a thickness ranging from about 1 mm to about 15 mm.

3. The method of claim 1 wherein the tissue to be replaced or augmented is located in the shoulder rotator cuff.

4. The method of claim 1 wherein the tissue to be replaced or augmented is a ligament of the knee selected from the group consisting of the cruciate anterior, cruciate posterior, collateral lateral, and medial ligaments.

5. The method of claim 1 wherein the damaged tissue to be replaced or augmented was the result of a acromioclavicular separation.

6. The method of claim 1 wherein the tissue to be replaced or augmented is a lateral collateral ligament of the ankle.

7. The method of claim 1 wherein the tissue to be replaced or augmented is a large tendon.

8. The method of claim 7 wherein the tissue to be replaced or augmented is selected from the group consisting of the achilles, quadriceps and patellar tendons.

9. The method of claim 1 wherein the tissue to be replaced or augmented is a small tendon.

10. The method of claim 9 wherein the tissue to be replaced or augmented is selected from the group consisting of the flexor and extensor tendons of the hand.

* * * * *